United States Patent
Umemura et al.

(10) Patent No.: US 7,785,260 B2
(45) Date of Patent: Aug. 31, 2010

(54) ULTRASONOGRAPH

(75) Inventors: Shin-ichiro Umemura, Hachioji (JP); Yuichi Miwa, North Bethesda, MD (US); Takashi Azuma, Kawasaki (JP); Takashi Sugiyama, Nagareyama (JP); Hiroshi Kuribara, Abiko (JP)

(73) Assignee: Hitachi Medical Corporation, Tokyo (JP)

( * ) Notice: Subject to any disclaimer, the term of this patent is extended or adjusted under 35 U.S.C. 154(b) by 417 days.

(21) Appl. No.: 10/482,789

(22) PCT Filed: Jun. 5, 2002

(86) PCT No.: PCT/JP02/05558

§ 371 (c)(1),
(2), (4) Date: Jul. 9, 2004

(87) PCT Pub. No.: WO03/049618

PCT Pub. Date: Jun. 19, 2003

(65) Prior Publication Data

US 2004/0243000 A1 Dec. 2, 2004

(30) Foreign Application Priority Data

Dec. 12, 2001 (JP) .............................. 2001-378074

(51) Int. Cl.
*A61B 8/00* (2006.01)
(52) U.S. Cl. .................. 600/447; 600/437; 600/443; 600/458
(58) Field of Classification Search ......... 600/437–472, 600/473; 73/1.82, 703
See application file for complete search history.

(56) References Cited

U.S. PATENT DOCUMENTS 5,511,423 A * 4/1996 Sugiyama et al. ............. 73/602

(Continued)

FOREIGN PATENT DOCUMENTS

JP 55-26976 8/1978

(Continued)

OTHER PUBLICATIONS

Lewis Thomas, Patrick Phillips, Robert Steins, Greg Holley and Kathy Quiroz, "Acuson Agent Detection Imaging, a New High Resolution Technique for Imaging Levovist and Other Contrast Agents", $2_{nd}$ International Kyoto Symposium on Ultrasound Contrast Imaging, Oct. 2000 (Proceedings, p. 83).

*Primary Examiner*—Brian Casler
*Assistant Examiner*—Amanda Lauritzen
(74) *Attorney, Agent, or Firm*—Stites & Harbison PLLC; Juan Carlos A. Marquez, Esq.

(57) ABSTRACT

An ultrasonograph capable of generating a transmission beam comprising a main beam having a uniform width over a wide range in an ultrasonic wave propagation direction by one-time transmission of an ultrasonic pulse. A weighted mean value of a plurality of transmission delay time values corresponding to focal lengths of transmission pulse waves having a plurality of focal points which are set in the ultrasonic wave propagation direction is calculated for each of elements constituting a transmission aperture and used as the delay time. The curvature of a transmitted wave front is close to a short focal length in the center portion of the transmit aperture and is close to a long focal length in the peripheral portion. Thus, a transmission beam including a relatively narrow main beam with a uniform width over a wide range in the ultrasonic wave propagation direction can be generated.

1 Claim, 10 Drawing Sheets

U.S. PATENT DOCUMENTS

| | | | |
|---|---|---|---|
| 5,579,768 A * | 12/1996 | Klesenski | 600/442 |
| 5,608,690 A * | 3/1997 | Hossack et al. | 367/138 |
| 5,675,554 A * | 10/1997 | Cole et al. | 367/138 |
| 5,997,480 A * | 12/1999 | Sumanaweera et al. | 600/454 |
| 6,056,693 A * | 5/2000 | Haider | 600/443 |
| 6,104,670 A * | 8/2000 | Hossack et al. | 367/7 |
| 6,228,031 B1 * | 5/2001 | Hwang et al. | 600/447 |
| 6,277,073 B1 * | 8/2001 | Bolorforosh et al. | 600/437 |
| 6,277,075 B1 * | 8/2001 | Torp et al. | 600/443 |
| 6,312,383 B1 * | 11/2001 | Lizzi et al. | 600/437 |
| 6,312,386 B1 * | 11/2001 | Bolorforosh et al. | 600/447 |
| 6,315,723 B1 * | 11/2001 | Robinson et al. | 600/443 |
| 6,328,695 B1 * | 12/2001 | Vammen et al. | 600/442 |
| 6,423,007 B2 * | 7/2002 | Lizzi et al. | 600/458 |
| 6,432,056 B1 * | 8/2002 | Cooley et al. | 600/443 |
| 6,517,489 B1 * | 2/2003 | Phillips et al. | 600/458 |
| 6,626,833 B2 | 9/2003 | Kawagishi et al. | |
| 6,780,152 B2 * | 8/2004 | Ustuner et al. | 600/443 |
| 6,873,716 B1 * | 3/2005 | Bowker et al. | 382/128 |
| 2002/0042577 A1 * | 4/2002 | Hatangadi et al. | 600/459 |
| 2004/0181152 A1 * | 9/2004 | Zhang et al. | 600/437 |
| 2007/0038091 A1 * | 2/2007 | Shiki | 600/437 |
| 2007/0293764 A1 * | 12/2007 | Umemura et al. | 600/459 |

FOREIGN PATENT DOCUMENTS

| | | |
|---|---|---|
| JP | 7-163569 | 12/1993 |
| JP | 10-155793 | 12/1996 |
| JP | 2001-245889 | 3/2000 |

* cited by examiner

ULTRASONOGRAPH

TECHNICAL FIELD

The present invention relates to an ultrasonograph for obtaining an image of the inside of a subject such as a living body by transmitting/receiving an ultrasound to/from the subject.

BACKGROUND ART

An ultrasonograph that transmits/receives a pulsed ultrasound to/from a living body and acquires an image of the inside of the living body is widely used in medical diagnosis. It is ideal to set focal points in the transmission/reception of the ultrasound for all of points in a living body in an image acquisition target range, from the viewpoints of both resolution and the S/N ratio of an ultrasound image.

As for reception, with recent advance of the digital circuit technology, in an electronically focused scanner, dynamic focusing of gradually increasing the focal length in accordance with lapse time since transmission of an ultrasound pulse become possible. By the dynamic focusing, images at all of points in a living body in a range of propagation of the ultrasound pulse can be acquired every transmission. Therefore, without sacrificing image acquisition speed, an ultrasound image having excellent resolution and a high S/N ratio can be obtained because of appropriate reception conditions with respect to all of points in a living body within the image acquisition target range.

As for transmission, however, the dynamic focusing performed in reception cannot be carried out. In the case of image capturing as described above, the transmit aperture is narrowed and focus is loosely achieved, thereby increasing the depth of focus (depth of field) by sacrificing the improvement in lateral resolution by a transmit beam. In such a manner, generally, increase in the necessary number of transmission times is suppressed, and image acquisition speed is assured. To partially compensate the drawback of the image acquisition mode, it is common to employ an apparatus configuration capable of selecting a mode between an image acquisition mode of giving a priority to both resolution and an S/N ratio in the region of interest while sacrificing resolution and an S/N ratio on the outside of the region of interest by adjusting the transmit focal length to the region of interest in a specific distance and by setting the transmit aperture to be relatively wide to emphasize the effects of the transmit focusing, and a mode of acquiring an image of high resolution and a high S/N ratio over the whole target range while gradually changing the transmit focal length at the cost of image acquisition speed.

Also in the field of ultrasonograph following an X ray and MRI, recently, a contrast agent is becoming a necessary component. The properties of a contrast agent for an X ray or MRI do not change irreversibly due to an action of either an electromagnetic wave emitted, a magnetic field applied, or the like for image acquisition, whereas a stabilized microbubble-based ultrasound contrast agent may collapse when the intensity of ultrasound emitted for imaging exceeds a certain level. The contrast enhancement dissipates after the collapse and lapse of sufficient time. However, there is also a contrast agent of a kind of which contrast enhancement conspicuously increases immediately after the shells for stabilization collapse.

It raises a new technical problem on the transmit focusing. Specifically, when a single focal length is set and waves are transmitted, changes in the intensity of ultrasound in the propagation direction are not uniform. Only in an area near the focal length, a contrast agent collapses and a relatively strong echo signal is generated at the time of the collapse. Alternately, when the transmit aperture is simply narrowed, the transmit focusing is broaden, and the intensity of ultrasound increases so as to obtain a signal of the contrast agent in a wide range in the propagation direction, by one-time transmission, the contrast agent in a range where a receive beam is not set at the time of the transmission also collapses. It becomes impossible to obtain an echo signal in the range by the following transmission.

As a conventional technique which solves at least a part of the problem, a method of setting a plurality of transmission focal points in an ultrasonic pulse propagation direction, overlapping wave fronts corresponding to the focal points at the same phase in the center portion of the transmit aperture, and transmitting the ultrasonic pulses simultaneously is reported in "2nd International Kyoto Symposium on Ultrasound Contrast Imaging (Proceedings, p. 83, October, 2000)". Spread in the time direction of a transmission pulse according to the method is small in the center portion of the transmit aperture in a manner similar to the case where the overlap transmission is not performed. The spread increases toward the periphery direction of the aperture, and the waveform becomes the same as that of the result of interference between the transmission signals corresponding to different focal points. Therefore, the waveform of the transmission pulse has to vary little by little from element to element in the transmit aperture. In an area around each of the focal points, the components to be focused to other focal points become acoustic noise in the azimuth direction. The reason why such acoustic noise does not simply become a problem in imaging using a microbubble-based contrast agent is considered as follows.

Originally, an echo signal from the stabilized microbubble-based contrast agent includes many of second harmonic components each having a frequency twice as high as that of a transmission signal due to reflection by a microbubble with the property as a non-linear oscillator. In order to discriminate the echo signal from the contrast agent from an echo signal from the peripheral tissue by using the fact that an image is often formed by the second harmonic components extracted from the echo signals. The amplitude of the second harmonic component generated from microbubbles is proportional to the square of the amplitude of a transmission signal, in contrast with the case where the amplitude of a fundamental wave component is proportional to that of a transmission signal. Therefore, it can be considered that, as compared with formation of an image by using the fundamental wave component, the acoustic noise level of a transmission beam is less important and, on the contrary, the uniformity of the thickness of a main beam is more important. Also from the property of microbubbles that when the amplitude of a transmission signal exceeds a certain level, the microbubble collapses, the uniformity of the width of a range with a transmission signal exceeding the level is considered to be more important than acoustic noise at a low level.

In the reported conventional method, a plurality of transmission pulse waves having focal points which are set in the ultrasound propagation direction are added in the sound pressure, that is, a drive voltage direction with respect to each of elements constructing the transmit aperture, thereby obtaining drive waveforms of the elements. In the method, since transmission signals corresponding to different focal points interfere each other, to prevent canceling off, the number of focal points to be set cannot be increased to several points or more. As a result, the uniformity in the ultrasound propagation direction of the width of the main beam formed is limited, and the control on the transmission waveforms of the elements is also complicated.

DISCLOSURE OF THE INVENTION

In view of such circumstances, an object of the present invention is to provide an ultrasonograph capable of generating a transmission beam including a main beam having uniform width over a wide range in the ultrasound propagation direction by one-time transmission of an ultrasonic pulse.

According to a method of the invention, a weighted mean value of a plurality of transmission delay time values corresponding to focal lengths of transmission pulse waves having a plurality of focal points which are set in the ultrasound propagation direction is obtained for each of elements constituting a transmit aperture, and the transmission pulse wave is actually transmitted with the value obtained as the delay time.

As the weight used for obtaining the delay time mean value, first, a transmission effective aperture width according to each transmission focal length is selected, and a weight in the direction of the transmit aperture realizing the width is calculated and is used in the direction of the focal length. It is most typical to select a transmission effective aperture width according to each transmission focal length so that the effective transmit F number is constant. However, in the case where ultrasonic scan lines are slightly deviated and are not parallel to each other like an echo image formed by a convex array transducer, it is desirable to finely adjust the effective transmit aperture width so that the main beam width as a function of a focal length is proportional to the interval of ultrasound scan lines. As the result, the curvature of a wave front of a wave transmitted is close to that of the wave front of a short focal length in the center portion of the transmit aperture, and is close to that of the wave front of a long focal length in the peripheral portion. Consequently, a non-cylindrical wave front is formed.

Thus, a transmission beam including a relatively narrow main beam with a uniform width over a wide range in the ultrasonic wave propagation direction can be generated by one-time transmission of an ultrasonic pulse by giving transmit waveforms which are almost the same except for the delay time and aperture weighting to the elements in the transmit aperture.

As described above, in the method of the invention, the amplitude of weighting and the delay time for transmit focusing are changed from element to element, but the waveform itself is not changed. Consequently, a number of transmit focal points can be sufficiently finely set in the ultrasound propagation direction without being influenced by interference between transmit signals corresponding to different transmit focal points. It is therefore expected that a transmit beam having higher uniformity in the width of the main beam can be generated. Since the waveform itself is common to the elements, such a transmit beam can be generated by relatively easy control.

By the method, an ultrasonograph suitable for acquiring an ultrasonic image by using a microbubble contrast agent can be realized. Also in image acquisition which does not use a contrast agent, an ultrasonic image having relatively high lateral resolution can be formed without sacrificing image acquisition speed.

BEST MODE FOR CARRYING OUT THE INVENTION

An embodiment of the invention will be described hereinbelow with reference to the drawings.

Figure 1:
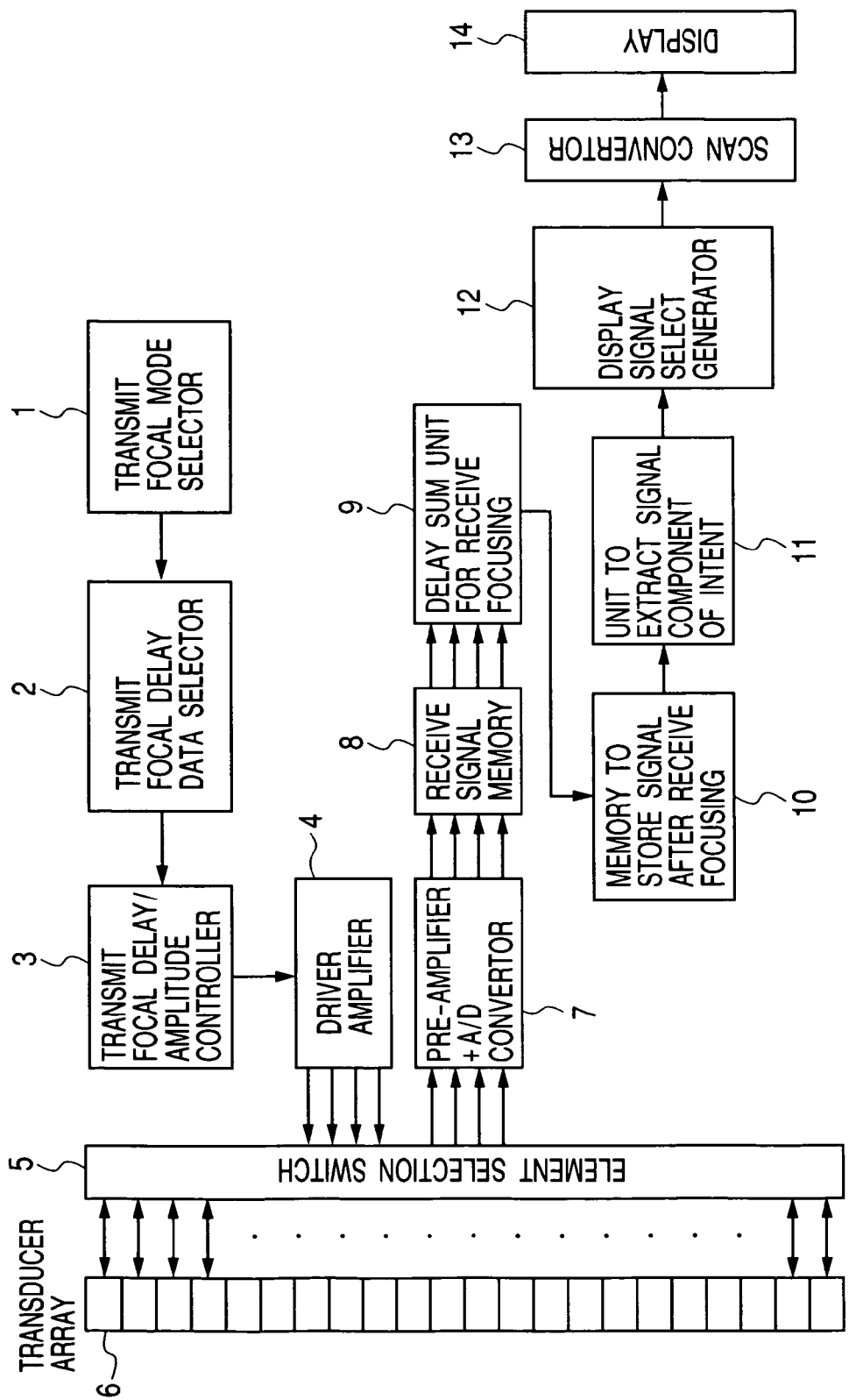
FIG. 1 is a block diagram showing the configuration of an ultrasonograph as an embodiment of the invention.

FIG. 1 is a block diagram showing a typical configuration of an apparatus acquired by applying the invention to an ultrasonic diagnostic system based upon a pulse-echo method.

A transmit focus mode selector 1 selects transmission of either a transmit beam having a uniform width in an ultrasound propagation direction or a transmission beam having resolution and an S/N ratio which are excellent only around a specific focal length. Based on the selection, a transmit focus delay data selector 2 selects corresponding transmit focus delay data and transmit aperture weight data.

A transmit focal delay and amplitude controller 3 supplies an input to a drive amplifier 4 at a timing controlled by giving a controlled amplitude to a transmit waveform on the basis of the data. An output of the drive amplifier 4 is transmitted to an element selected by an element selecting switch 5 from elements constructing a transducer array 6, thereby forming a transmit wave front having directivity.

A transmit ultrasonic pulse sent from the transducer array 6 to a living body in such a manner is reflected by an organ of the living body and a contrast agent, a part of the pulse returns to the transducer array 6 and is received by the elements constructing the transducer array 6. A signal of the element selected by the element selecting switch 5 from the receive signals is amplified by a preamplifier 7. The amplified signal is A/D converted, and the resultant data is temporarily stored in a receive memory 8.

More specifically, generally, immediately after the preamplifier, the signal passes a TGC amplifier which is controlled so that an amplification factor gradually increases with time elapsed since transmission and is A/D converted. This is a process for maintaining the amplitude of a signal at the inlet of an A/D converter to be within a predetermined range by compensating a decrease in the amplitude of a reception signal, which is almost proportional to time elapsed from transmission in correspondence with attenuation of the ultrasound propagating through the living body, which is almost proportional to a propagation distance. By the process, deterioration in the signal dynamic range by quantization of the amplitude in A/D conversion is prevented. Further, as it is known, in addition to the above, by passing the signal through a bandwidth limiting filter before the A/D conversion, an aliasing caused by time base quantization in the A/D conversion can be prevented.

To acquire the directivity of a received wave, a kind of delay according to the position of each element is once given to a reception signal of the element stored in the memory 8 and, after that, delayed signals are added so as to obtain a convergence effect. A receive focal delay sum unit 9 executes the processing. An optimum value of delay time to be given to a signal of each element is varied according to the focal length of a received wave.

An optimum value of the focal length of a received wave for acquiring a satisfactory pulse echo image increases in proportion to time elapsed since transmission and acoustic velocity. Therefore, it is desirable to employ a dynamic focus receiving method of varying delay time to be given to a signal of each element in accordance with time elapsed since transmission. This method can be relatively easily realized by control in reading or writing in a configuration as shown in FIG. 1 that a signal received by each element is temporarily written to the memory and is read again and the signals are added.

In B mode of a general ultrasonograph, the amplitude is acquired by a detecting process from a signal obtained by adding delay for converging a received wave and is logarithmically compressed to be a display signal. A display signal selector/generator 12 shown in the diagram executes this processing, a scan converter 13 converts the display signal to a two-dimensional image or a three-dimensional image according to circumstances and a display 14 displays the image on a CRT or a liquid crystal display according to circumstances.

In a harmonic imaging method, a nonlinear component is extracted from a signal obtained by adding delay for converging a received wave by a unit 11 to extract a signal of interest, and similar processing is performed on the component to be a display signal. Hereby, a pulse echo image in which the distribution of a stabilized microbubble-based contrast agent having higher nonlinear reflectivity as compared with a living tissue is enhanced can be acquired.

In the most basic harmonic imaging method, higher harmonics generated by nonlinear effect are separated from a fundamental wave by a bandpass filter and are extracted. Nonlinear component extracting methods that do not depend upon a bandpass filter include a pulse inversion method and an amplitude modulation method. In the amplitude modulation method, the amplitude is varied in a plurality of ways and transmitted. The principle of the nonlinear component extraction is that the amplitude of an echo linear component of a received wave is proportional to that of a transmitted wave, however, the amplitude of a nonlinear component is not proportional to that of the transmitted wave. A case of using two kinds of amplitudes will be described as an example. A converged signal obtained by transmitting a signal having a first amplitude a1 is temporarily recorded in a memory 10 to store the signal after receive focusing. A converged signal obtained by transmitting a signal having a second amplitude a2 is multiplied by a1/a2. The difference between the resultant signal and the signal recorded in the memory 10 is calculated, thereby eliminating a linear component and extracting a nonlinear component. In a normal amplitude modulation method, a1 and a2 are positive real numbers. On the other hand, the pulse inversion method uses a pair of real numbers whose absolute values of which signs a1 and a2 are inverted are equal.

A method of calculating the transmit focus delay data and the transmit aperture weight data selected by the transmit focal delay data selector 2 at the time of transmitting a transmit beam having a uniform width in the ultrasound propagation direction will be described specifically hereinbelow. A case of forming a main beam having a uniform width over the range of a focal length from 20 mm to 100 mm in image capturing by a linear array transducer of a transmission ultrasonic frequency of 2 MHz will be described as an example.

A number of focal lengths are set at sufficiently fine intervals of 1 mm in a range of a distance from 20 mm to 100 mm, and aperture weight An(L) to be given to the n-th element in the transmit aperture is calculated in correspondence with a focal length L.

Figure 2:
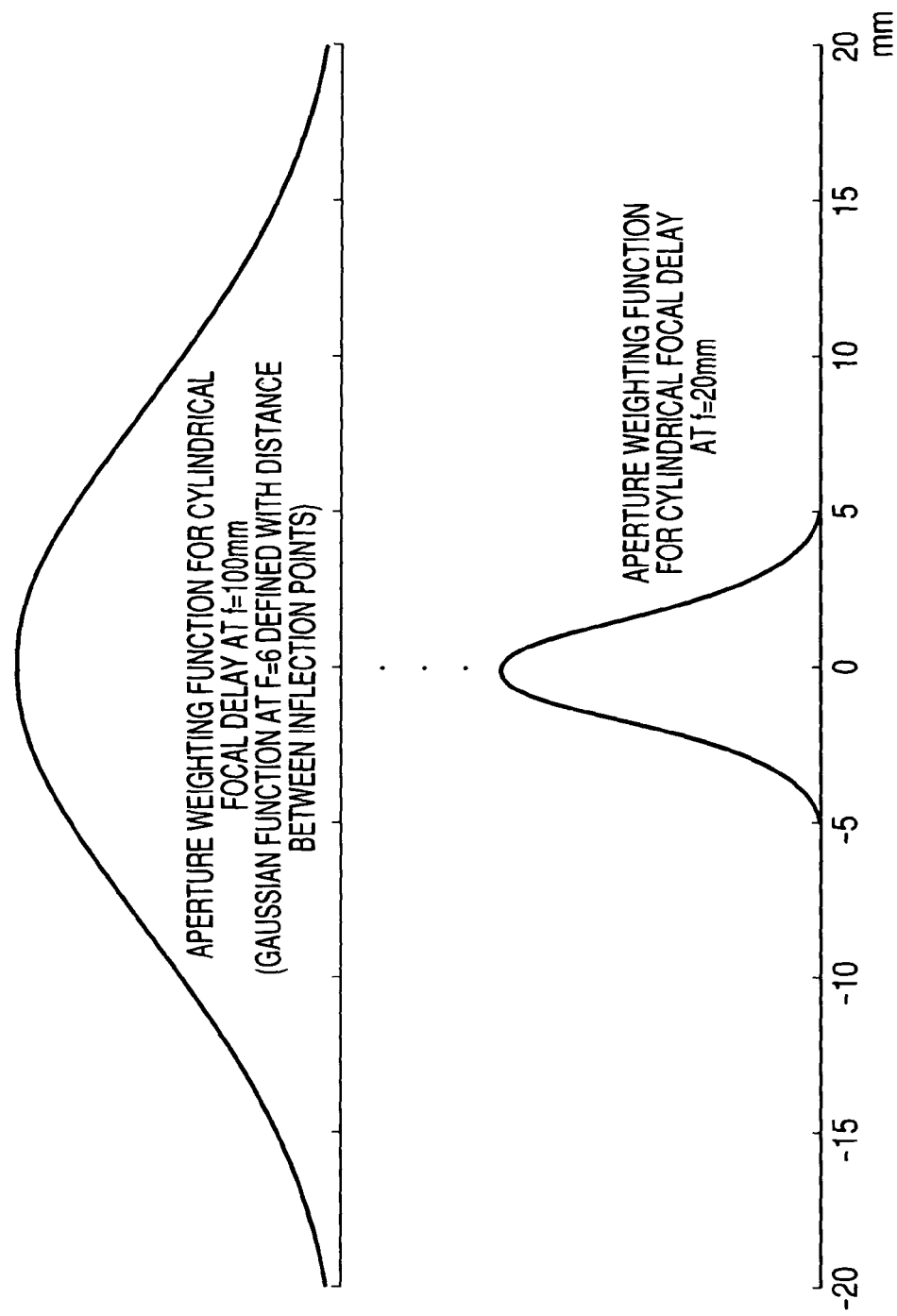
FIG. 2 is a diagram showing an example of a transmit aperture weighting function used for calculation of weighted mean delay time.

In FIG. 2, as an example, An (20 mm) and An (100 mm) are plotted as functions of coordinates on the transmit aperture. As the aperture weighting function, a Gaussian function is selected, which has a preferable characteristic such that the shape does not change even by diffraction during propagation since the shape does not change by Fourier transform. A width is selected in correspondence with the focal length L so that an F number defined by the interval between two inflection points becomes 6.

A weighted means value Un (transmit delay time) is obtained with respect to each element by the following equation by using the calculated aperture weight An(L) on the basis of delay time Tn(L) to be given to the element for transmit focusing with respect to each focal length L. The delay time is used for transmission of an ultrasonic pulse.

$$Un = \int Tn(L)An(L)dL / \int An(L)dL \qquad (1)$$

It is natural to obtain and use the aperture weighting for transmitting an ultrasonic pulse by calculating Bn (transmit aperture weight) derived by normalizing the denominator of the right side of the equation (1) as follows.

$$Bn = \int An(L)dL / \int dL \qquad (2)$$

Figure 3:
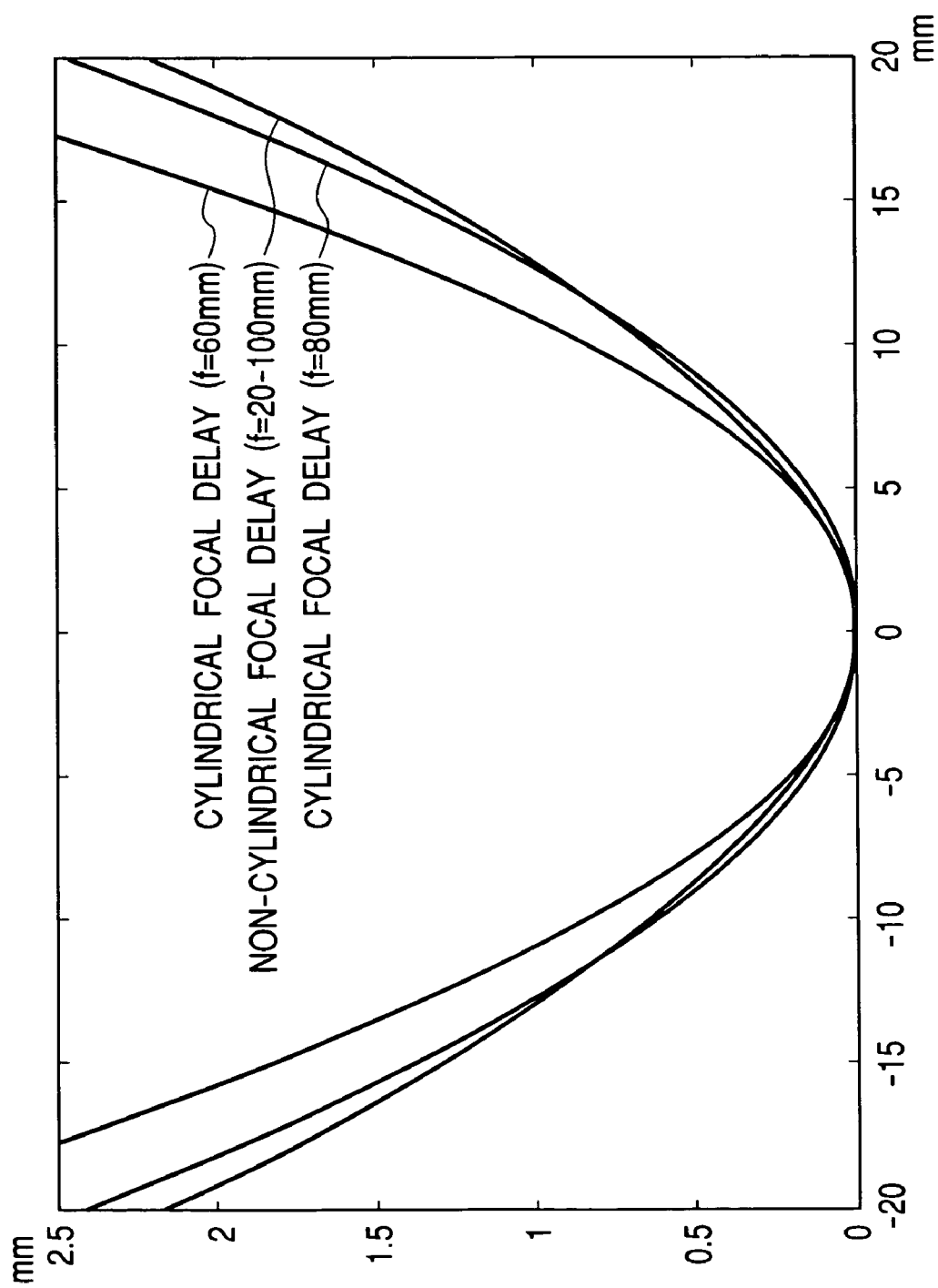
FIG. 3 is a diagram showing transmit delay time by non-cylindrical focusing obtained by weighted mean.

FIG. 3 is a plot of the transmit delay time Un by non-cylindrical focusing obtained as described above in comparison with transmit delay time Tn (60 mm) and transmit delay time Tn (80 nm) by normal spherical focusing of focal lengths of 60 mm and 80 mm. The vertical axis denotes propagation distance calculated by multiplying the transmit delay time with acoustic velocity. The radius of curvature as a whole is larger than Tn (80 mm), but the radius of curvature in a center portion is smaller than Tn (60 mm).

Figure 4:
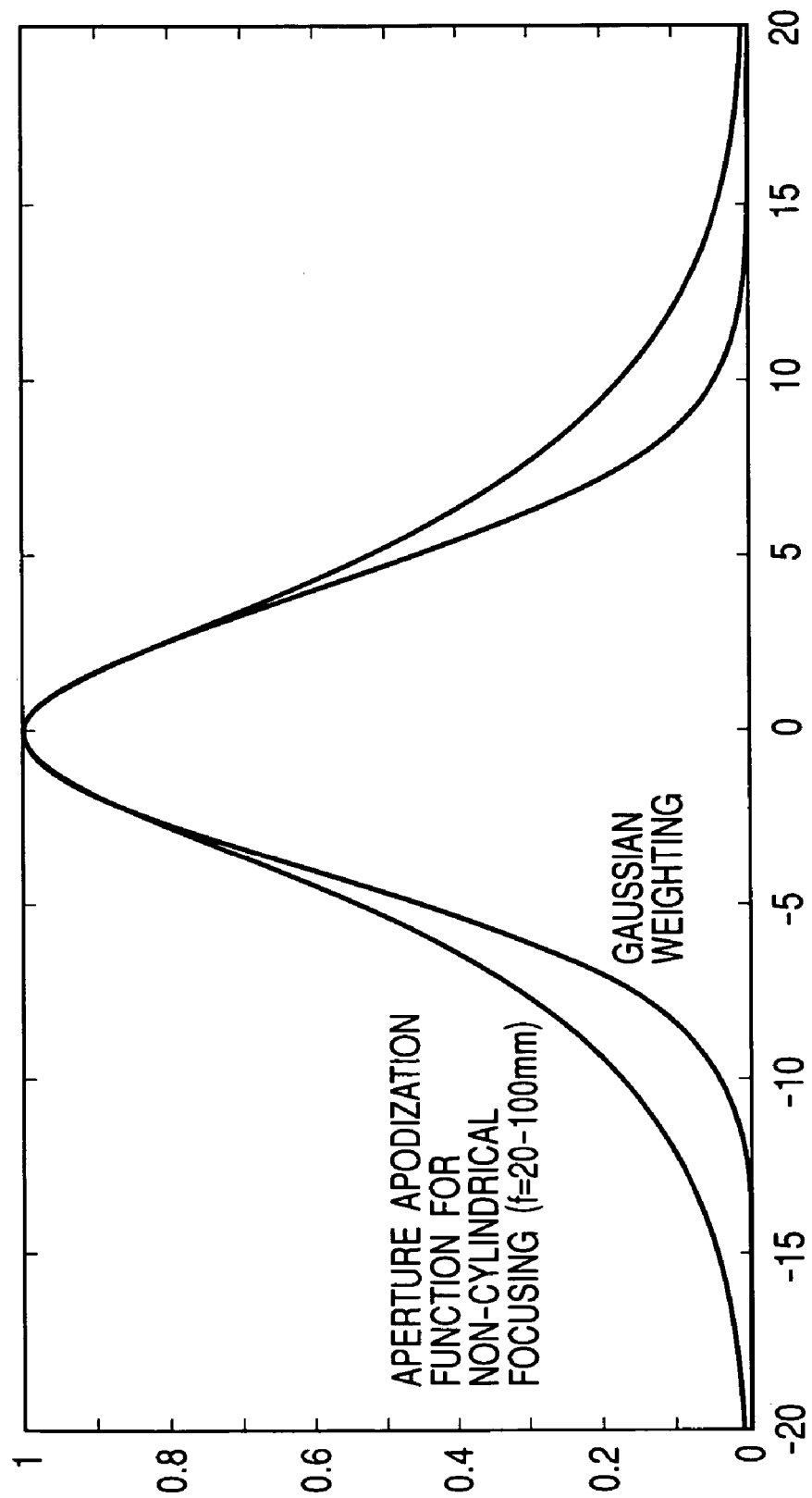
FIG. 4 is a diagram showing a transmit aperture weight in non-cylindrical focusing obtained by weighted mean.

FIG. 4 is a plot of the transmit aperture weight Bn calculated as described above in comparisons with Gaussian function aperture weight An (60 mm). Although the weights in the center portion are similar to each other, the plot of the transmit aperture weight Bn has a wider bottom.

Figure 5:
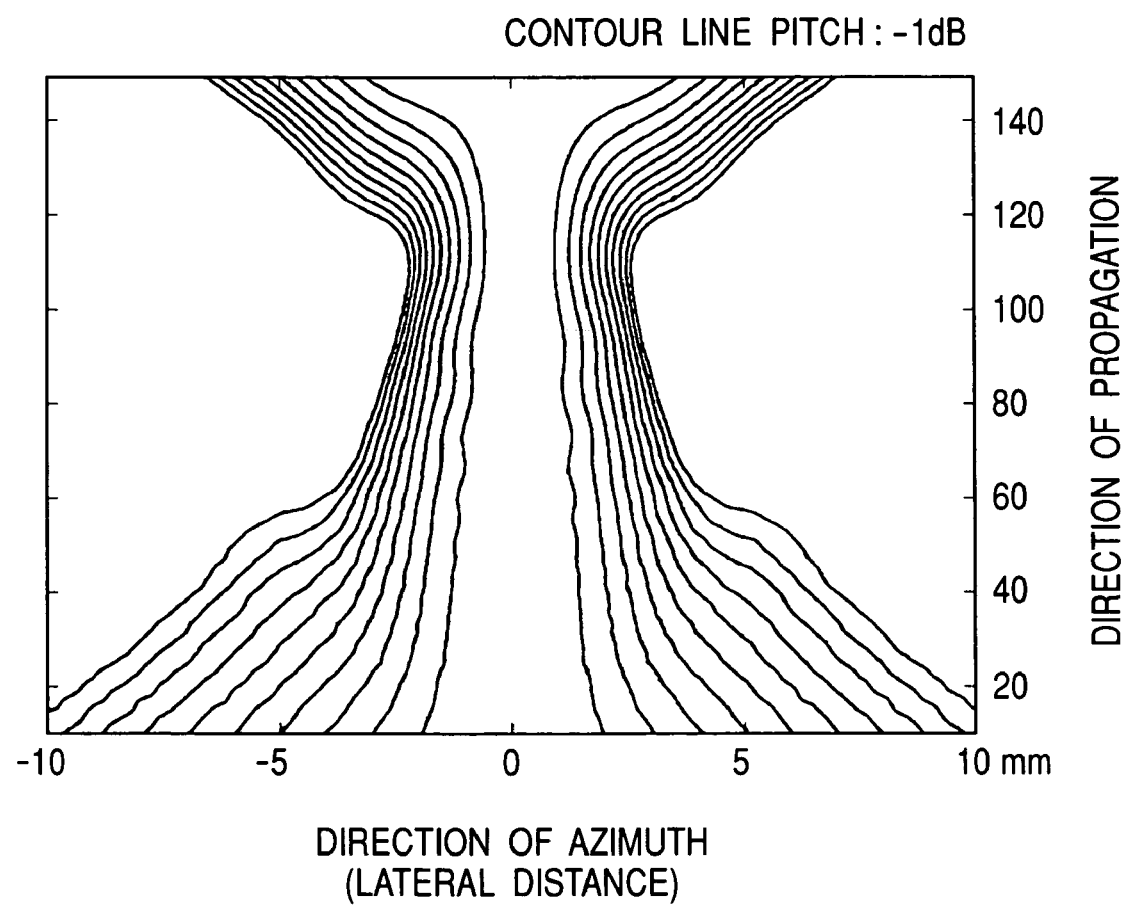
FIG. 5 is a diagram showing a transmit beam according to the invention, which is generated when an ultrasonic wave is transmitted using the transmit delay time and the transmit aperture weight obtained by the non-cylindrical focusing.

FIG. 5 is a contour map in increments of 1 dB formed by obtaining a transmission beam generated when an ultrasonic wave of a frequency of 2 MHz is transmitted by using the transmit delay time Un by non-cylindrical focusing and the transmit aperture weight Bn obtained as described above by numerical value calculation simulation, and plotting a range from the maximum value of the ultrasonic amplitude to −10 dB in each of distances in the propagation direction. In the case of forming a main beam having a uniform width in the range of propagation distance from 20 mm to 140 mm by using a transmit aperture of 48 mm, Un and Bn obtained by giving a weight of a Gaussian function of width so that the F number defined by the interval between the inflection points becomes 5 are applied.

Figure 6:
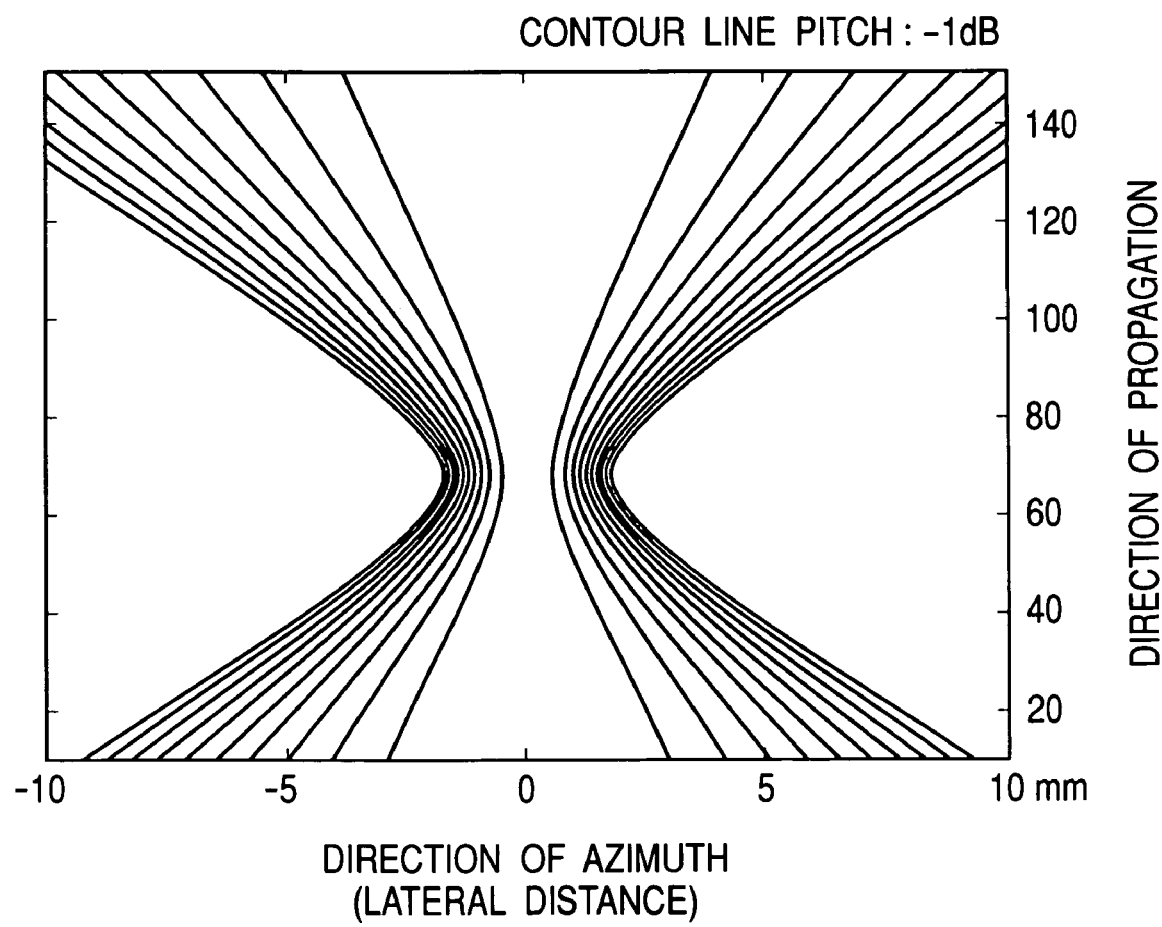
FIG. 6 is a diagram showing a transmit beam according to a prior art, which is generated when an ultrasonic wave is transmitted using the transmit delay time obtained by cylindrical focusing and a transmit aperture weight of a Gaussian function type.

In FIG. 6, a transmit beam having a focal length of 70 mm by normal cylindrical focusing is similarly plotted. As a transmit aperture weight, a Gaussian function of a width by which the F number defined by the interval between inflection points becomes 5 was used. In such a manner, while making the maximum transmit amplitude in the center portion of the aperture common, ultrasonic powers integrated in a transmit beam can be almost equalized.

In the transmit beam of FIG. 6, the width of the main beam at each of focal lengths of 20 mm and 120 mm is widened about three times as large as the width at the focal length 70 mm. In contrast, in FIG. 5, a transmit beam having an almost uniform width from the distance 20 mm to 130 mm is formed by applying the method of the invention.

Figure 7:
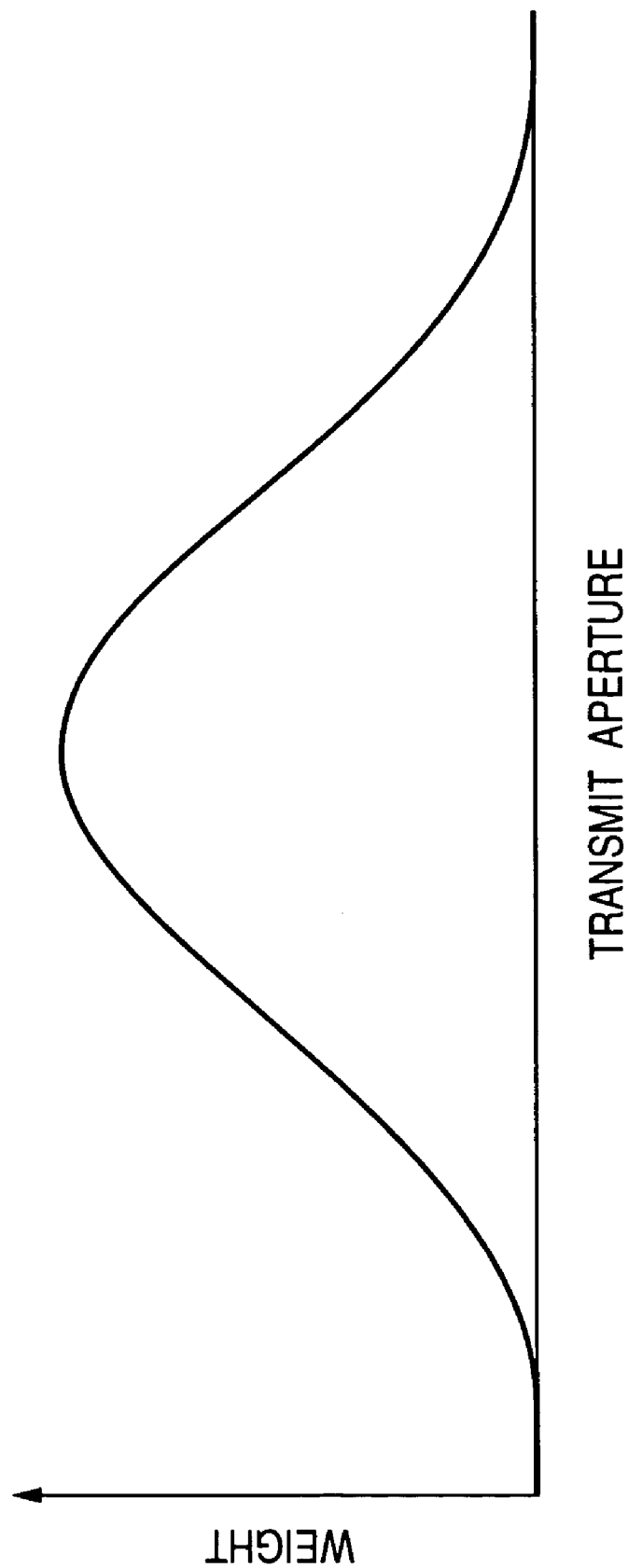
FIG. 7 is a diagram showing a transmit aperture weighting function obtained by multiplying a Hanning function having a zero point at an end of the transmit aperture with a Gaussian function.
Figure 8:
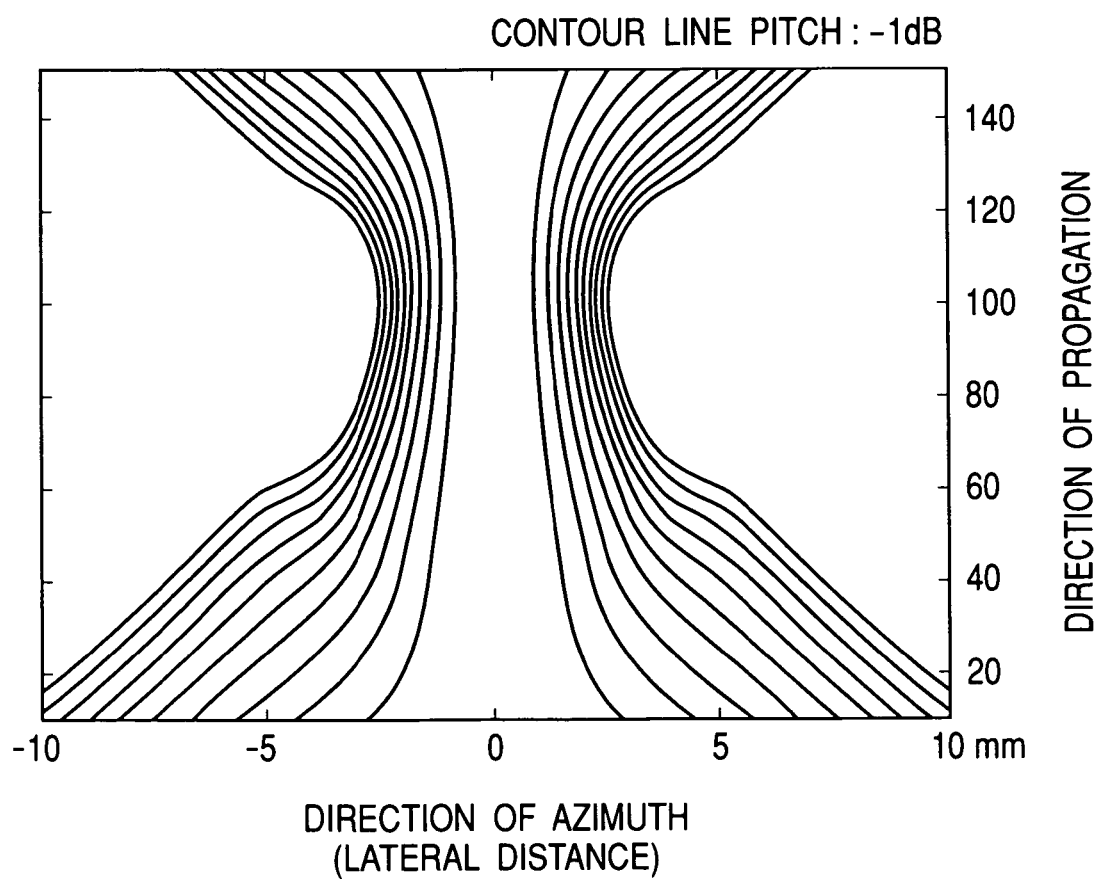
FIG. 8 is a diagram showing a transmit beam according to the invention, which is generated when an ultrasonic wave is transmitted using transmit delay time and the transmit aperture weight of FIG. 7 obtained by the non-cylindrical focusing.

However, in the main beam width of FIG. 5, small ripples are seen in the propagation direction for the reason that the transmit aperture weight Bn is limited by the transmit aperture width 48 mm and it causes a step in the transmit weight at an end of the aperture. A transmit aperture weighting function as shown in FIG. 7 is therefore generated by multiplying a Hanning function in which the weight becomes zero just at an end of the aperture with a Gaussian function having a proper width so that the ultrasonic power integrated in the transmit beam becomes almost equal. By using the transmit aperture weighting function in place of Bn, a transmit beam as shown in FIG. 8 can be generated. A smooth beam having no ripples as in FIG. 5 is formed over a range from the distance 20 mm to 140 mm.

Figure 9:
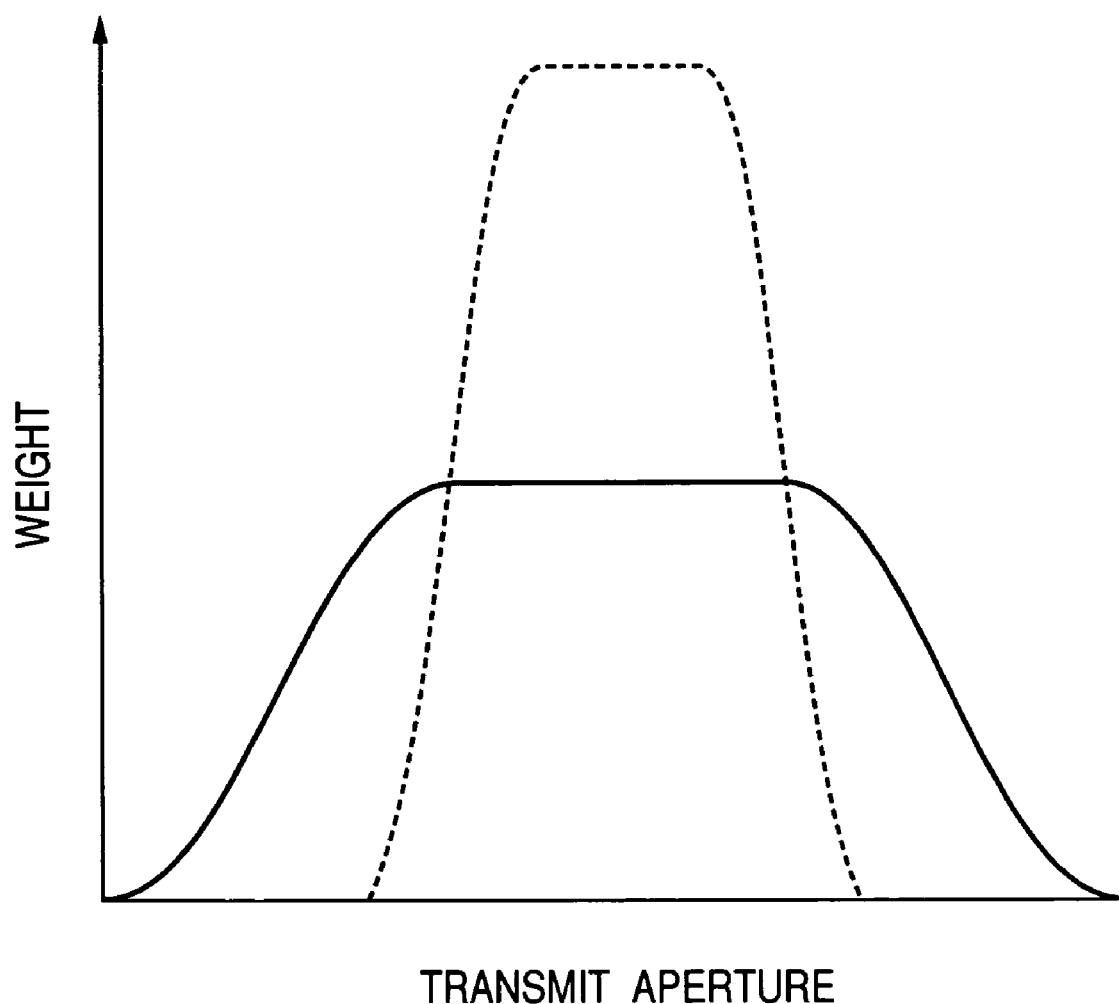
FIG. 9 is a diagram showing another example of the transmit aperture weighting function used for calculating weighted mean delay time.
Figure 10:
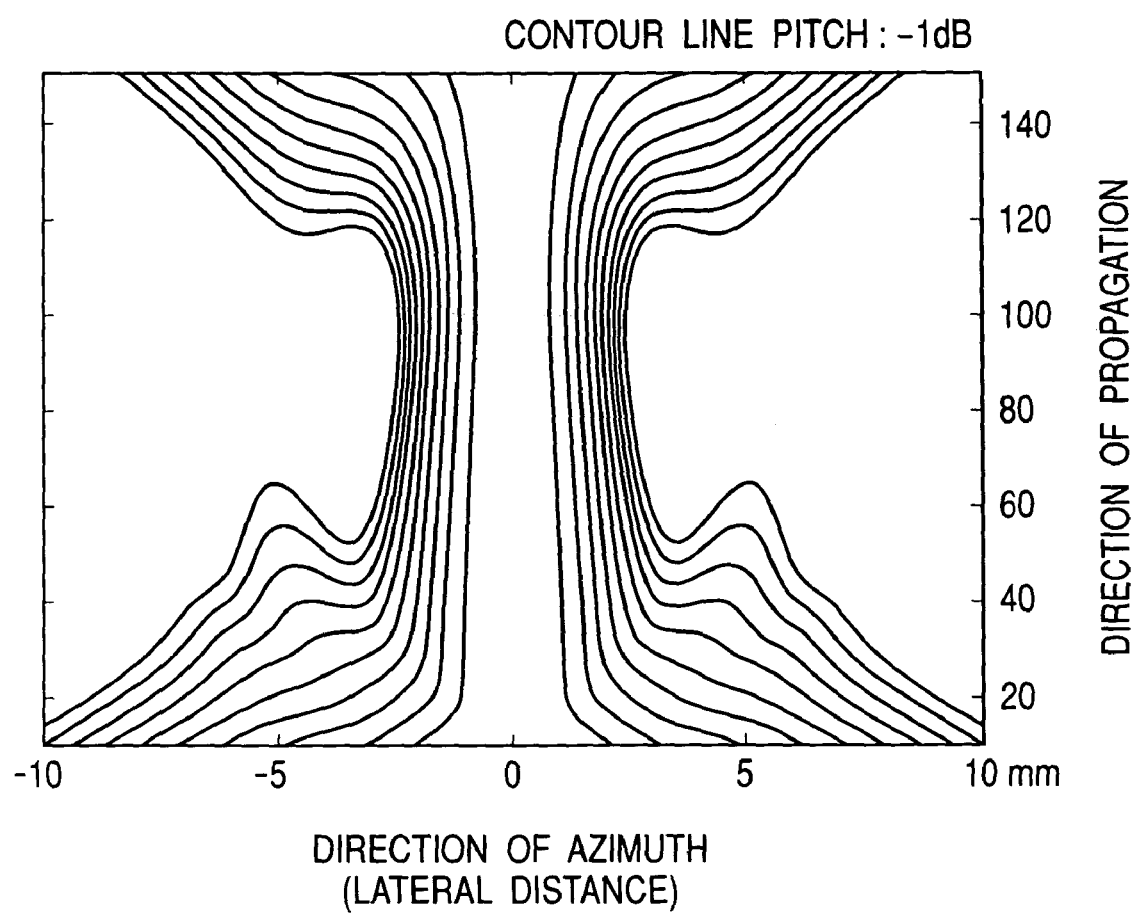
FIG. 10 is a diagram showing a transmit beam obtained by non-cylindrical focusing of the invention, which is generated when an ultrasonic wave is transmitted using the non-cylindrical transmit delay time calculated by using the transmit aperture weighting function of FIG. 9 and a transmit aperture weight of FIG. 7.

In addition, when a weight which is inversely proportional to the focal length is given to, in place of the Gaussian function, a flat-headed Hanning function having a flat portion in the center portion where the Hanning function is the maximum value as shown in FIG. 9 and the resultant is used as the aperture weighting function An to be given to Tn in order to generate the transmit delay time Un, a transmit beam as shown in FIG. 10 can be formed. In this case, the center portion which is ⅓ of the overall width of the flat-headed Hanning function is made flat, and a width is given so that the F number defined by the interval of inflection points, that is, a half-value width becomes 3. Consequently, the area of An is made constant irrespective of the focal length. As a result, a transmit beam having a main beam width which is uniform over the range from the distance 20 mm to 140 mm is formed.

Although the case of making the transmit beam width uniform over the range from the distance 20 mm to the 140 mm from the transducer has been described in the foregoing embodiment, the invention is not limited to the case. With a configuration of preliminarily recording a plurality of sets of non-cylindrical focus data, reading it, and using it as transmission control data, the range can be easily varied according to the purpose of diagnosis.

In an ultrasonograph using conventional single transmit focusing, the depth of the transmit focusing is often indicated by a triangle sign or the like on a screen on which an ultrasonic echo image is displayed. In the apparatus using non-cylindrical transmit focusing of the present invention, in place of such a sign indicating only one point, a bar, a double-headed arrow, or the like indicating the range of transmit focusing in the depth direction is used. With the configuration, an easy-to-use ultrasonograph can be realized.

The waveform of a transmit wave front based on the present invention described above can be measured as follows. For example, two needle-shaped hydrophones are disposed very close to the surface of the transducer array which is put in water, and transmit pulses generated from the transducer array are received by the hydrophones and observed. One of the needle-shaped hydrophones receives the transmit pulse while being gradually moved in the array direction and the time difference between waveforms received by the two needle-shaped hydrophones is recorded as a function of a travel amount, thereby enabling the curvature of the transmit wave front to be measured.

As described above, according to the invention, a weighted mean value of a plurality of transmission delay time values corresponding to focal lengths of transmission pulse waves having a plurality of focal points which are set in the ultrasonic wave propagation direction is calculated for each of elements constituting a transmission aperture and used as delay time. Waves are transmitted with the weighted mean value as delay time. As a result, the curvature of a wave front of a wave transmitted is close to that of the wave front of a short focal length in the center portion of the transmit aperture, and is close to that of the wave front of a long focal length in the peripheral portion. Consequently, a non-cylindrical wave front is formed. Thus, a transmission beam including a relatively narrow main beam with a uniform width over a wide range in the ultrasonic wave propagation direction can be generated by transmission of an ultrasonic pulse of once by giving almost the same waveform except for delay time and the aperture weight to the elements in the transfer aperture.

Thus, an ultrasonograph particularly suitable for ultrasound image acquisition using a microbubble-based contrast agent can be realized. Also in image acquisition using no contrast agent, without sacrificing image acquisition speed, an ultrasound image having relatively high lateral resolution can be formed.

INDUSTRIAL APPLICABILITY

The present invention realizes the ultrasonograph capable of forming a transmission beam including a main beam having a uniform width over a wide range in the ultrasound propagation direction by transmission of an ultrasonic pulse of once. Therefore, the invention is very significant in medial and industrial fields.

The invention claimed is:

1. A method of obtaining an image of the inside of a subject by transmitting/receiving an ultrasonic pulse to/from the subject, the method comprising:
   transmitting an ultrasonic pulse from a transmit aperture of a transducer array, the ultrasonic pulse having a short focal length in a center portion of the transmit aperture, a long focal length in a peripheral portion of the transmit aperture of said transducer array of the transmit aperture, and a non-cylindrical wavefront continued smoothly over an entirety of the transmit aperture; and
   forming a transmission beam having a propagation distance range of substantially uniform widths each perpendicular to an ultrasound propagation direction of the ultrasonic pulse by one transmission of the ultrasonic pulse, the propagation distance range being variable in the ultrasound propagation direction.

* * * * *